United States Patent [19]

Chow

[11] 4,435,418

[45] Mar. 6, 1984

[54] 5-PHENYLETHENYLBENZIMIDAZOLES

[75] Inventor: Alfred W. Chow, Radnor, Pa.

[73] Assignee: SmithKline Beckman Corporation, Philadelphia, Pa.

[21] Appl. No.: 449,350

[22] Filed: Dec. 13, 1982

[51] Int. Cl.³ ............... A01N 43/52; C07D 235/30; C07D 235/32
[52] U.S. Cl. ............................ 424/273 B; 548/306
[58] Field of Search .................. 548/306; 424/273 B

[56] References Cited

U.S. PATENT DOCUMENTS

| 3,657,267 | 4/1972 | Van Gelder et al. | 548/306 |
| 3,856,811 | 12/1974 | Daum et al. | 548/306 |
| 4,230,868 | 10/1980 | Paget et al. | 548/306 |

Primary Examiner—Richard Raymond
Attorney, Agent, or Firm—William H. Edgerton; Richard D. Foggio; Alan D. Lourie

[57] ABSTRACT

New 2-acylamino-5-phenylethenylbenzimidazoles have been prepared and found to have anthelmintic activity. A species of the invention is methyl [5-(1-phenylethenyl)-1H-benzimidazol-2-yl]carbamate.

14 Claims, No Drawings

5-PHENYLETHENYLBENZIMIDAZOLES

This invention relates to new compounds which have structures characterized by being a 2-acylaminobenzimidazole which is substituted, at the 5-position of its benzene ring, with 1-phenylethenyl. The compounds have anthelmintic activity.

BACKGROUND OF THE INVENTION

Certain 5-acyl-2-benzimidazolylcarbamates have anthelmintic activity, U.S. Pat. No. 3,657,267. Mebendazole, a marketed member of this group, is methyl (5-benzoyl-1H-benzimidazol-2-yl)carbamate. Of course, such compounds do not have the 1-phenylethenyl substituent which distinguishes the structures of the compounds of this invention.

DESCRIPTION OF THE INVENTION

The new compounds of this invention are represented by the following structural formula:

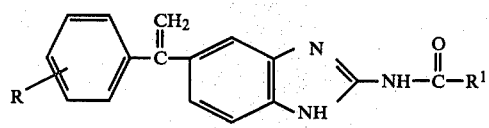

in which:

R is hydrogen, halo such as fluoro, chloro or bromo, methoxy, methyl or methylthio.

R¹ is lower alkyl of 1-4 carbons or lower alkoxy of 1-4 carbons.

"Lower alkyl" represents straight or branched alkyl groups as well as cycloalkyl groups of 3 or 4 ring members.

A subgroup of the compounds of formula I are those in which R is H or 4-fluoro and R¹ is cyclopropyl or methoxy.

The compounds of this invention are prepared by a several step sequence of chemical reactions.

in which R is as defined above and Alk represents a straight, branched or cyclic lower alkyl group of 1-4 carbons which is stable as known to the art.

The first step of the reaction comprises the Wittig reaction which is carried out by reacting a Wittig reagent, such as ylid, for example, a methylenetriphenylphosphorane, or a compound which forms such a ylid in situ, with an optionally trisubstituted benzophenone (II). The benzophenone starting materials are known in the literature. The reaction is conveniently carried out by reacting (methyl)triphenylphosphonium bromide in the presence of sodium hydride with the selected 3-nitro-4-aminobenzophenone in an inert organic solvent, such as dimethylsulfoxide, at an elevated temperature until the reaction is substantially complete.

The resulting 1-phenylethylene compound (III) is then subjected to a mild reducing agent which is suitable for nitro groups, for example, sodium sulfhydrate in aqueous alcohol, to give the optionally substituted 1-(3,4-diaminophenyl)-1-phenylethylene (IV).

The diamine is cyclized to the end product benzimidazole directly by using cyanamide in a one-pot reaction in the presence of an acylating agent, such as a lower alkyl chloroformate or a lower alkanoyl halide to give the desired product (I). The reaction is, usually, carried out in aqueous alkali-acetone-ethanol in the cold. As an alternative, the diamine is reacted with a bis-alkanoyl-S-methylisothiourea in acidic methanol at reflux. Finally, the 5-(1-phenylethenyl)-2-aminobenzimidazole (V) may be isolated, optionally, from the reaction of the diamine with cyanogen bromide and, then, N-acylated with the noted acylation agents, such as lower alkyl chloroformate or a lower alkanoyl halide or anhydride, in the presence of a liquid tertiary organic amine.

The compounds of this invention have general anthelmintic activity against parasites living in the digestive tract of various mammalian hosts such as swine, cattle, dogs, goats, horses, sheep or cats. Examples of such parasites are the nematodes, such as round worms, hookworms or pinworms, the cestodes, such as the tapeworms, as well as the flukes. The anthelmintic ac- Sequence A

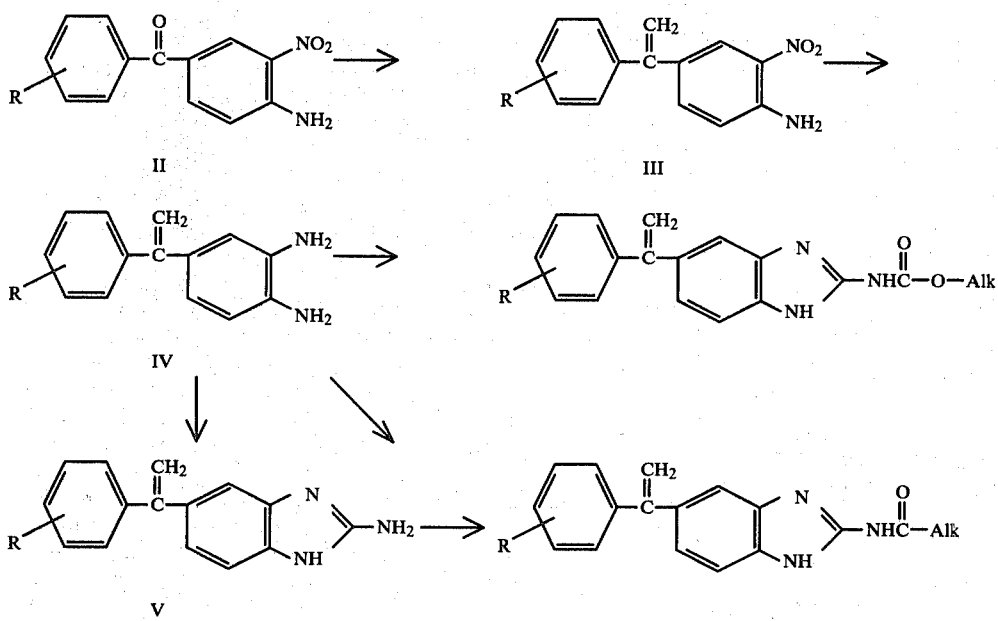

tivity is observed following oral administration of a tablet, drench, bolus or other pharmaceutical, animal feed or veterinary composition adapted for oral administration.

For example, the disclosed compounds are generally effective in clearing mice of worm infections for laboratory purposes, among others: *Syphacia obvelata* and *Aspicularis tetraptera* (mouse pinworm), *Nematospiroides dubius* (mouse hookworm) and the migratory stages of *Ascaris suum*.

Other susceptible helminths include Toxocara canis, found in naturally infested dogs. Also, parasitic to this host are *Ancylostoma canium, Trichuris vulpis* (whipworm) and Physalaptera ssp.

These compounds are efficacious against parasites of pigs, such as the migratory stages of *Ascaris suum*, thus preventing the development of verminous pneumonia.

Among the gastrointestinal parasites in sheep and cattle which are susceptible are *Haemonchus contortus, Ostertagia* spp., *Trichostrongylus* spp., *Nematodirus* spp., *Trichuris ovis,* Cooperia spp., *Strongyloides papillosus,* Bunostomum spp., Chabertia sp. and Oesophagostomum spp.

In practice, the active 5-(1-phenylethenyl)benzimidazole compound is, usually, formulated with a nontoxic pharmaceutical veterinary or feed carrier therefor to give the anthelmintic compositions of this invention. The carrier may be either a standard animal feed composition which is based on a feed premix whole feed composition or an orally ingestible anthelmintic carrier for the active ingredient, for example, a drench, a dispersible tablet or powder, or a gelatin capsule; or it may be a pharmaceutically acceptable diluent or excipient of the kind normally used in the production of veterinary or human medicaments, for example, maize, starch, terra alba, lactose, sucrose, calcium phosphate, gelatin, talcum, stearic acid, magnesium stearate, dextrin, agar, pectin or acacia.

Exemplary of liquid carriers are peanut oil, olive oil, sesame oil and water. Similarly, the carrier or diluent may include a time delay material, such as glyceryl monostearate or glyceryl distearate alone or with a wax.

The compositions are advantageously made up in a dosage unit form adapted for the desired frequency and mode of administration. Thus, for the preferred oral administration, the dosage unit may take the form of a suspension, top dressing, tablet, packaged powder, bolus or encapsulated dispensible powder. The quantity of active ingredient in each dosage unit will be such that one or more units are required for each therapeutic administration.

Where tableting is used, the resulting tablets may then be coated with methyl methacrylate to form an enteric coating, i.e., a coating which is substantially insoluble in gastric secretion but substantially soluble in intestinal fluids.

The compositions, thusly prepared using a anthelmintic, but nontoxic, quantity chosen from the range of 2-15 mg/kg., are administered, usually orally, to an infected or susceptible host from 1-5 times daily for curative or prophylactic anthelmintic activity. Preferably, one dose daily is used.

Exemplary of the anthelmintic activity of this new series of compounds are the following results[a]:

[a] Determined by the methods outlined in V. J. Theodorides "Anthelmintics: From Laboratory Animals to the Target Species" Chapter 5, Chemotherapy of Infectious Diseases, pages 71-93, Ed. H. H. Gadebusch, C.R.C. Press, 1976.

A. Compound of Example 3

Methyl[5-(1-phenylethenyl)-1H-benzimidazol-2-yl]-carbamate

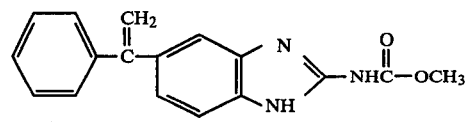

| Nematospiroides dubius Mouse | Fasciola Hepatica-Mouse[b] | Fasciola Hepatica-Sheep[c] |
|---|---|---|
| 86% at 0.006% | 83/19 at 0.05% | 95% at 5 mg/kg |
| 31% at 0.05% | 50/0 at 0.05% | |
| 0% at 0.025% | | |
| 51% at 0.1% | | |

[b] Percent by weight of diet. The first figure is an index of hepatic pathology, the second is percent reduction of worm burden.
[c] Milligrams of compound per kilogram of body weight. In addition, the first compound, A, was found not to be embryotoxic, a serious side effect which many anthelmintic benzimidazoles possess.

B. Compound of Example 4

N-[5-(1-phenylethenyl)-1H-benzimidazol-2-yl]-cyclopropanecarboxamide

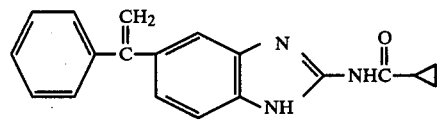

14% at 0.025%    67/0 at 0.025%

The following examples illustrate specific aspects of the invention which may be employed in preparing and using the compositions of the invention but are not intended to limit the scope of the invention described hereinbefore. Degrees of temperature are in Centigrade unless otherwise noted.

EXAMPLE 1

| Typical Cattle Bolus | |
|---|---|
| Methyl [5-(1-phenylethenyl)-1H-benzimidazol-2-yl]carbamate | 0.02 grams |
| Calcium Phosphate | 2.5 grams |
| Maize Starch | 0.54 grams |
| Talcum | 0.14 grams |
| Gum Arabic | 0.15 grams |
| Magnesium Stearate | 0.5 grams |

The calcium phosphate and the anthelmintic compound are thoroughly mixed, and the mixture reduced to a particle size finer than 60 mesh. About one-half of the starch is added, as an aqueous paste, and the resulting mixture granulated. The granules are passed through a 10 mesh screen and dried at 110°-130° F. for about eight hours. The dried materials are then passed through a No. 16 mesh screen. The guar gum and the balance of the starch are added and the mixture thoroughly blended. Finally, the remainder of the ingredients are added and the entire mass thoroughly mixed and compressed into a bolus. The magnesium stearate, talcum and gum acacia are of a particle size to pass a No. 10 mesh screen.

EXAMPLE 2

| Sheep Drench | Parts by Weight |
| --- | --- |
| Methyl [5-(1-phenylethenyl)-1H-benzimidazol-2-yl]carbamate | 20 |
| Terra Alba English | 65.5 |
| Tragacanth, U.S.P. | 3.0 |
| Sodium Lauryl Sulfate | 1.5 |
| Water | |

The above solid components are thoroughly mixed, giving a water dispersable powder. This powder can be directly admixed with water in concentrations on the order of 10.5 g. of powder to 5 cc. of water.

EXAMPLE 3

Sodium hydride (2.4 g., 0.1 mole) was suspended in dimethyl sulfoxide (50 ml.) and heated at 70° under nitrogen until evolution of hydrogen gas ceased (approximately ½ hour). To this suspension at room temperature was added a solution of (methyl)triphenylphosphonium bromide (35.7 g., 0.1 mole) in dimethyl sulfoxide (100 ml.). The greenish cloudy solution was stirred at ambient temperature for fifteen minutes. To this was, then, added (4-amino-3-nitrophenyl)phenylmethanone (12.1 g., 0.05 mole). The resulting dark red solution was heated at 90° for 18 hours under nitrogen. The reaction mixture was, then, cooled and diluted with water (500 ml.). The pH was adjusted to 7.0 by the addition of 3 N hydrochloric acid. This solution was, then, extracted with ethyl ether (2×150 ml.). The combined organic extracts were washed with water (500 ml.), dried over sodium sulfate and evaporated to dryness. The resulting dark oil was chromatographed over silica gel, yielding an orange solid; 1-(4-amino-3-nitrophenyl)-1-phenylethylene: 7.7 g., 64% yield, m.p. 136°-7°.

1-(4-Amino-3-nitrophenyl)-1-phenylethylene (7.7 g., 0.032 mole) was dissolved in refluxing ethanol (450 ml.). To this was added, dropwise, a solution of sodium sulfhydrate (38.5 g., 0.45 mole) in water (110 ml.). The resulting solution was refluxed overnight. The solution was diluted with water (1 l.), cooled, and filtered yielding 1-(3,4-diaminophenyl)-1-phenylethylene: 5.6 g., 83% yield, m.p. 109°-110°.

1-(3,4-Diaminophenyl)-1-phenylethylene (3.2 g., 0.015 mole) was dissolved in methanol (100 ml.). To this was added water (32 ml.), 1,3-bis (methoxycarbonyl)-S-methylisothiourea (3.2 g., 0.015 mole), and acetic acid (3 drops). The reaction solution was, then, refluxed for 1.5 hours, cooled and the product collected by filtration. This tan solid was dissolved in warm methanol (100 ml.) and 3 N hydrochloric acid (50 ml.). The solution was cooled, filtered, and, then, neutralized to pH 7.0 by a 5% sodium bicarbonate solution. The precipitate was collected by filtration, yielding methyl [5-(1-phenylethenyl)-H-benzimidazol-2-yl]carbamate: 4.0 g., 91% yield, m.p. 217°-8°. Anal. Calcd. for $C_{17}H_{15}N_3O_2$, C, 69.61; H, 5.15; N, 14.33; Found: C, 69,46; H, 5.20; N, 14.11.

EXAMPLE 4

A mixture of 3.6 g. (15 mmole) of 2-amino-5-(1-phenylethenyl)-benzimidazole [prepared from the diamine described in Example 3 by using cyanogen bromide as described by J. H. Wikel, et al., J. Med. Chem. 23 368 (1980)], 3.12 g. (30 mmole) of cyclopropane carboxylic acid chloride and 100 ml. of pyridine was allowed to react at room temperature, quenched and the product isolated to give 3.4 g. (75%) of N-[5-(1-phenylethenyl)-1H-benzimidazol-2-yl]cyclopropanecarboxamide, hydrate, m.p. 199°-202°.

Anal. Calcd. for $C_{19}H_{17}N_3O.1/8$ $H_2O$: C, 74.67; H, 5.68; N, 13.75. Found: C, 74.47; H, 5.72; N, 14.03.

Using acetyl chloride gives the corresponding acetamide, using propionyl chloride gives the corresponding propionamide and using propylchloroformate gives propyl [5-(1-phenylethenyl)-1H-benzimidazol-2-yl]carbamate.

EXAMPLE 5

Susbstituting (4-amino-3-nitrophenyl)3-methylphenylmethanone, (4-amino-3-nitrophenyl) 4-methoxyphenylmethanone, (4-amino-3-nitrophenyl) 4-fluorophenylmethanone or (4-amino-3-nitrophenyl) 2-chlorophenylmethanone [all prepared as in A. H. M. Raeymaekers et al., Arzneim-Forsch 28 58 (1978)] in the method of Example 3 gives methyl 5-[1-(3-methylphenyl)ethenyl]-1H-benzimidazol-2-yl carbamate, methyl 5-[1-(4-methoxyphenyl)ethenyl]-1H-benzimidazol-2-yl carbamate, methyl 5-[1-(4-fluorophenyl)ethenyl]-1H-benzimidazol-2-yl carbamate and methyl 5-[1-(2-chlorophenyl)ethenyl]-1H-benzimidazol-2-yl carbamate respectively.

What is claimed is:

1. A chemical compound of the formula:

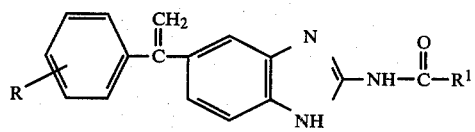

in which:

R is hydrogen, halo, methyl, methoxy or methylthio; and $R^1$ is lower alkyl of 1-4 carbons, cycloalkyl of 3-4 ring members or lower alkoxy of 1-4 carbons.

2. The compound of claim 1 in which R is hydrogen or 4-fluoro and $R^1$ is methoxy.

3. The compound of claim 1 being methyl [5-(1-phenylethenyl)-1H-benzimidazol-2-yl]carbamate.

4. The compound of claim 1 being methyl 5-[1-(4-fluorophenyl)ethenyl]-1H-benzimidazol-2-yl]carbamate.

5. The compound of claim 1 being N-[5-(1-phenylethenyl)-1H-benzimidazol-2-yl]-cyclopropanecarboxamide.

6. An oral anthelmintic composition having activity against nematodes, cestodes or flukes comprising an anthelmintic but non-toxic quantity of a compound of the formula:

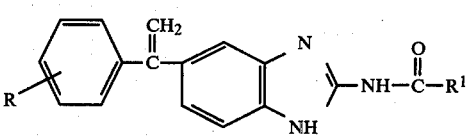

in which:

R is hydrogen, halo, methyl, methoxy or methylthio; and $R^1$ is lower alkyl of 1-4 carbons, cycloalkyl of 3-4 ring members or lower alkoxy of 1-4 carbons combined with a pharmaceutical, animal feed or veterinary carrier.

7. The composition of claim 6 in which the compound is methyl [5-(1-phenylethenyl)-1H-benzimidazol-2-yl]carbamate and the quantity is selected from the range of 2–15 mg/kg.

8. The composition of claim 6 in which the compound is methyl 5-[1-(4-fluorophenyl)ethenyl]-1H-benzimidazol-2-yl]carbamate and the quantity is selected from the range of 2–15 mg/kg.

9. The composition of claim 6 in which the compound is N-[5-(1-phenylethenyl)-1H-benzimidazol-2-yl]cyclopropane carboxamide.

10. The method of producing anthelmintic activity in hosts infected with, or susceptible to, helminthic infections comprising administering orally to said hosts an anthelmintic, but non-toxic, quantity of a compound of the formula:

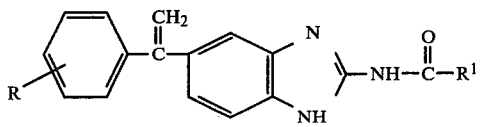

in which:
R is hydrogen, halo, methyl, methoxy or methylthio; and
$R^1$ is lower alkyl of 1–4 carbons, cycloalkyl of 3–4 ring members or lower alkoxy of 1–4 carbons.

11. The method of claim 10 in which the quantity of active compound is from the range of 2–15 mg/kg administered orally to animals once daily.

12. The method of claim 10 in which the compound is methyl 5-(1-phenylethyenyl)-benzimidazol-2-yl carbamate.

13. The method of claim 10 in which the compound is methyl 5-[1-(4-fluorophenyl)ethenyl]-1H-benzimidazol-2-yl carbamate.

14. The method of claim 10 in which the compound is N-[5-(1-phenylethenyl)-1H-benzimidazol-2-yl]cyclopropanecarboxamide.

* * * * *